United States Patent [19]
Palmer et al.

[11] Patent Number: 4,491,798
[45] Date of Patent: Jan. 1, 1985

[54] SYSTEM FOR MEASURING CONDUCTIVITY OF A LIQUID

[76] Inventors: James K. Palmer, 134 Fel Mar Dr.; Robert K. Janeway, 33 Verde Dr., both of San Luis Obispo, Calif. 93401

[21] Appl. No.: 332,874

[22] Filed: Dec. 21, 1981

[51] Int. Cl.$^3$ .............................................. G01N 27/07
[52] U.S. Cl. .................................. 324/425; 324/442; 324/445
[58] Field of Search ............... 324/425, 439, 442, 445, 324/450, 442

[56] References Cited

U.S. PATENT DOCUMENTS

| | | | |
|---|---|---|---|
| 3,292,077 | 12/1966 | Sloughter | 324/445 |
| 3,417,329 | 12/1968 | Landis et al. | 324/445 |
| 3,470,465 | 9/1969 | Wushke | 324/442 |
| 3,531,252 | 9/1970 | Rivers | 324/439 |
| 4,220,920 | 9/1980 | Gross | 324/442 |

FOREIGN PATENT DOCUMENTS

| | | |
|---|---|---|
| 698190 | 10/1953 | United Kingdom . |
| 1001379 | 8/1965 | United Kingdom . |
| 1039223 | 8/1966 | United Kingdom . |
| 1085557 | 10/1967 | United Kingdom . |
| 1320876 | 6/1973 | United Kingdom . |
| 1585067 | 2/1981 | United Kingdom . |

*Primary Examiner*—Stewart J. Levy
*Attorney, Agent, or Firm*—Daniel C. McKown

[57] ABSTRACT

A system for assessing the effectiveness of a water softener or comparable liquid-processing apparatus whose effectiveness is related to the difference between the electrical conductivity of the liquid supplied to the apparatus and the electrical conductivity of the liquid that has passed through the apparatus includes two inductance loop conductivity sensors excited by a common signal generator. The outputs of the sensors, which typically include unwanted quadrature components, are applied directly to the inputs of a differential amplifier. The resulting difference signal is then applied to a detector that is gated by the common excitation signal, so as to produce a detected signal that is substantially unaffected by the unwanted quadrature components. In a preferred embodiment, each of the inductance loop conductivity sensors includes two electrodes connected by a conductor that links two toroids.

15 Claims, 3 Drawing Figures

SYSTEM FOR MEASURING CONDUCTIVITY OF A LIQUID

BACKGROUND OF THE INVENTION

1. Field of the Invention

The present invention is in the field of water treatment and particularly relates to a system for determining the effectiveness of a water softener or a similar water treating device.

2. The Prior Art

A water softener of the ion exchange type is typical of the type of apparatus the present invention is used to monitor. Such a water softener includes a chamber through which the water to be softened flows. The chamber contains a bed of pellets of an ion exchange resin. As the incoming hard water passes through the bed, the magnesium and calcium ions are exchanged for sodium ions which pass into the water, softening it.

With extended use the ion exchange bed becomes depleted of sodium ions, and the efficiency of the softener decreases. When the efficiency has decreased to the point where the water is not soft enough for the intended use, the ion exchange bed must be regenerated.

As the ion bed gradually becomes depleted and the treated water becomes less soft, the electrical conductivity of the treated water gradually decreases until ultimately it approaches the conductivity of the incoming untreated water.

The system of the present invention continually senses the conductivity of the untreated water and the conductivity of the treated water. When a freshly charged ion exchange bed is first put into use, the difference in the conductivities is greatest and is therefore designated as 100% efficiency. With use, the difference decreases and ultimately approaches zero.

Two major families of conductivity sensors have been identified in the prior art: the direct contact type of instrument and the inductance loop type of instrument. The system of the present invention employs a modified form of the inductance loop instrument.

U.S. Pat. No. 3,246,759, issued Apr. 19, 1960 to Matalon, describes a direct contact type of instrument in which electrodes are positioned in the resin bed and connected to a detection circuit. Current is impressed on the circuit and the amplitude of the current is responsive to the conductivity of the resin-water system between the electrodes. As the sodium ions of the resin are replaced by magnesium or calcium ions from the water, the conductivity of the resin-water system decreases and the current flow decreases accordingly. A major deficiency of direct contact instruments of this type is that the electrodes become contaminated over a period of time by the ions present in the water, thereby making accurate measurements over a period of time impossible. As mentioned above, the present invention employs a modified form of inductance-loop instrument.

In a typical inductance loop type of instrument, an exciting toroid and a pick-up toroid are juxtaposed in the water. An alternating voltage is applied to the exciting toroid, and this causes a weaker alternating voltage to be induced in the pick-up toroid because of the coupling provided between the toroids by a current loop in the water linking the toroids.

As will be discussed below, this type of instrument is susceptible to certain types of deficiencies which the system of the present invention overcomes.

In a technical paper entitled "A Probe Type Induction Conductivity Cell" by E. E. Aagaard and R. H. vanHaagen of Oceanic Instruments, Inc., Houghton, Wash., published around 1962, there are described circuits in which a transformer bridge couples a pair of toroids which are also coupled by the unknown conductivity of the liquid. The purpose of the transformer bridge is to enable a nulling type of operation that is implemented by a potentiometer in the bridge circuit. A capacitor is connected across the pick-up toroid to provide a tuned circuit which is more sensitive to the signal being nulled and which tends to filter out noise and to reduce null signal phase shift with respect to the exciting voltage. This is shown in FIG. 3 of the reference. In connection with FIGS. 5 and 6 of the reference, the authors mention that a small quadrature (reactive) component may be present in the bridge circuit and that this would interfere with obtaining a sharp null. They state that compensation for this reactive component may be made with a small variable capacitor connected across the poteniometer in the bridge circuit. While this expedient does permit the introduction of an opposing reactance, the adjustment is not automatic.

In U.S. Pat. No. 2,542,057 issued Feb. 20, 1951, Relis discusses the problem of spurious voltages being induced in the pick-up toroid. Relis attributes these spurious voltages partly to flux leakage from the exciting toroid intercepting the pick-up toroid and partly to capacitive coupling between the toroids. Relis' solution to this problem is to provide a voltage injecting network to supply a bucking voltage of adjustable phase and magnitude to nullify the spurious voltages. This solution requires that the system be calibrated prior to use by a time-consuming iterative procedure. The need for this procedure is eliminated by the system of the present invention.

SUMMARY OF THE INVENTION

The primary objective of the present invention is to provide a system for monitoring the effectiveness of a water softener or similar water treating device. This function is very important where large quantities of water are supplied to a boiler or vaporizer which would quickly become fouled by mineral deposits if the water softener proved ineffective.

In accordance with the system of the present invention, a fraction of the untreated water and a fraction of the treated water are diverted for use by the system. The diverted fraction of the untreated water is put through an extra length of conduit to provide a delay for the untreated water that is comparable to the delay experienced by the treated water in having gone through the water softener. Next, the treated and untreated fractions are put through a parallel-flow heat exchanger to ensure that both the treated and untreated water are at the same temperature. This is important because the conductivity of water varies with temperature. Thereafter, the treated water passes through a conductivity sensor and, in parallel, the untreated water passes through a separate conductivity sensor, as shown in FIG. 1.

In accordance with the system of the present invention, the outputs of the treated water sensor and the untreated water sensor are combined in a special circuit as shown in FIG. 1. The circuit consists of the elements shown within the dashed lines of FIG. 2. Thus, the outputs of the pick-up toroids of the sensors are preamplified and then fed to a differential amplifier. The latter produces an output that is proportional to the difference of its inputs. The difference signal is then applied to an active filter, amplified again, and applied to a synchronous detector. The output of the synchronous detector is applied to a d.c. amplifier to produce a signal suitable for operating a meter.

The resulting system has several advantages over those systems known in the prior art. The use of a synchronous detector eliminates the undesirable quadrature components without the need for intervention by the operator. Elimination of the undesirable quadrature components enhances the accuracy of measurement.

The accuracy of the system is further enhanced by taking the difference between the signals from the pick-up toroids prior to substantially amplifying the signal, instead of amplifying the toroid signals first and then taking the difference, as will be explained in greater detail below.

Thus, a number of features are combined according to the system of the present invention to achieve an instrument of superior accuracy. These features include provision of a transport delay for the fraction of the untreated water, the use of a parallel-flow heat exchanger, the use of a novel type of sensor, and an electronic signal processing circuit that employs a synchronous detector. Collectively, these features overcome the major problems associated with systems known in the prior art and result in a system of high accuracy and dependability.

The novel features which are believed to be characteristic of the invention, both as to organization and method of operation, together with further objects and advantages thereof, will be better understood from the following description considered in connection with the accompanying drawings in which several embodiments of the invention are illustrated by way of example. It is to be expressly understood, however, that the drawings are for the purpose of illustration and description only and are not intended as a definition of the limits of the invention.

DETAILED DESCRIPTION OF THE PREFERRED EMBODIMENT

Figure 1:
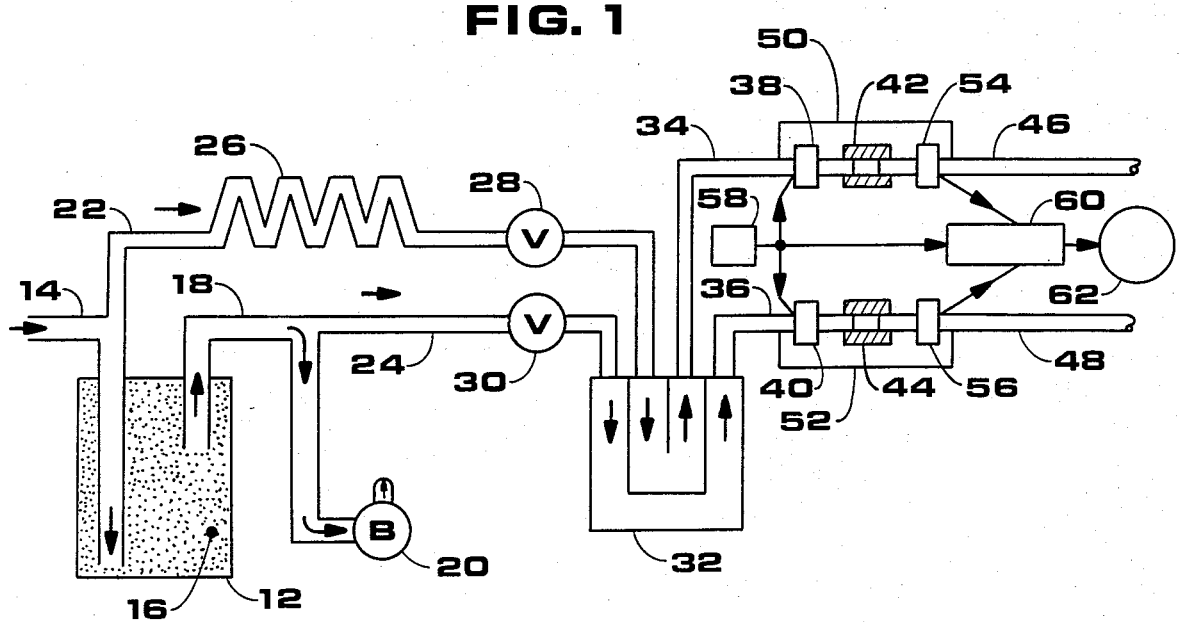
FIG. 1 is a diagram, partly hydraulic and partly electrical, illustrating the preferred embodiment of a system for monitoring the effectiveness of a water treatment apparatus in accordance with the present invention.

Turning now to the drawings, in which similar parts are denoted by like reference numerals throughout, there is shown in FIG. 1 a diagram of a system in accordance with a preferred embodiment of the present invention for monitoring the effectiveness of a water softener 12 or similar water treatment apparatus. Untreated water is brought into the water softener 12 through the pipe 14. Typically, the water softener 12 includes an ion exchange resin bed 16 through which the water percolates. The water issues from the water softener 12 as softened or treated water through the pipe 18, which conducts the softened water to a boiler 20. A small fraction of the untreated water is tapped from the pipe 14 into the pipe 22, and a small fraction of the treated water is tapped off from the pipe 18 into the pipe 24.

The system continually samples the conductivity of the treated water and simultaneously continually samples the conductivity of the untreated water. The difference in the conductivities is a measure of the effectiveness of the water softener 12. It is entirely possible that the hardness of the water entering through the pipe 14 may change unpredictably with time, and thus, for maximum accuracy it is necessary that the treated water sample and the untreated water sample be derived from water entering the water softener at a particular instant of time.

To make the measured samples contemporaneous, a transport delay 26 is included in the pipe 22, to compensate for the time required for the treated water sample to pass through the water softener 12. Thus, at any instant, the water samples passing through the valves 28 and 30 flowed from the pipe 14 at substantially the same instant. The purpose of the valves 28, 30 is to equalize, approximately, the flow through the pipes 24, 26. The valves 28, 30 are set initially, but require further adjustment only rarely.

The treated and untreated fractions in the pipes 22, 24 are next conducted into the parallel-flow heat exchanger 32. The fractions are not mixed in the heat exchanger, and parallel flow, rather than the more common opposed flow, is necessary to achieve the objective of the heat exchanger 32, which is to equalize the temperatures of the treated and untreated fractions. This is necessary if maximum accuracy is to be achieved, in view of the fact that the conductivity varies with the temperature. Thus, the samples being measured at any instant of time are at the same temperature as well as being contemporaneous. The untreated and treated fractions are conducted through a short distance to the conductivity sensing protion of the system through the pipes 34, 36 respectively.

A first exciting toroid 38 encircles the pipe 34 and a second exciting toroid 40 encircles the pipe 36. The pipes 34, 36 then terminate on the right hand side of the toroids 38, 40 as viewed in FIG. 1. The fractions continue to flow through the insulative sleeves 42, 44 and then into the pipes 46, 48 which are encircled by the toroids 54, 56 respectively. The insulative sleeves 42, 44 ensure that the opposing ends of the pipes 34, 46 and the opposing ends of the pipes 36, 48 are maintained in a predetermined spacing which does not necessarily have to be the same for the two flow paths. The conductivity is actually sensed in the water within the insulative sleeves 42, 44. The pipes 34, 46 are electrically connected by the conductor 50 as well as by a conductive path extending through the liquid sample within the insulative sleeve 42. Likewise, the pipes 36, 48 are connected by the conductor 52 as well as by a conductive path through the liquid within the insulative sleeve 44. An oscillator 58 applies an alternating current to the first and second exciting toroids 38, 40. In a preferred embodiment, the frequency of the alternating current is 20 kilohertz. The alternating current in the toroids 38, 40 induces an alternating current in the first and second pick-up toroids 54, 56, and these currents are applied to the signal processing circuit 60 which converts them to a readily perceptible form, such as a reading on the meter 62. In a preferred embodiment of the invention, the meter 62 is calibrated to show the efficiency of the water softener 12 as a percentage defined as 1.00 minus the ratio of the conductivity of the treated water to the conductivity of the untreated water.

Figure 2:
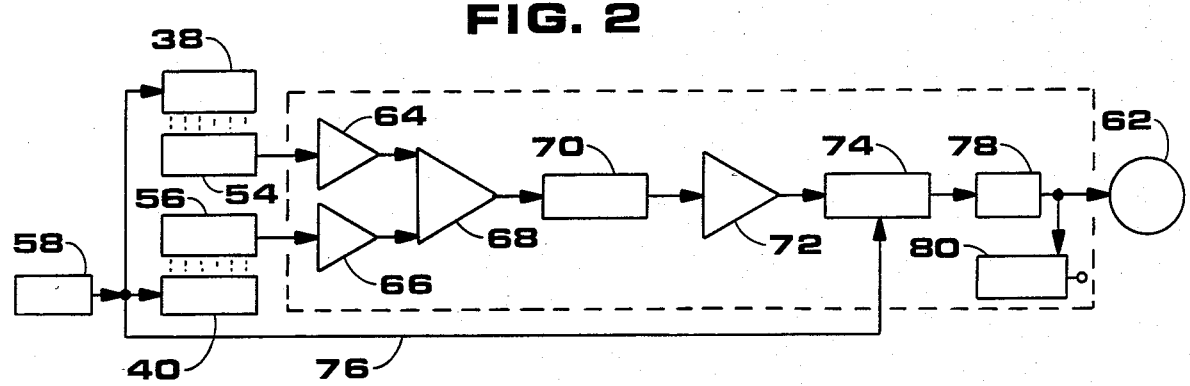
FIG. 2 is an electrical block diagram showing in greater detail the circuitry used in the system of FIG. 1; and, FIG. 3 is an electrical block diagram of a system for measuring the conductivity of a liquid in accordance with the present invention.

The signal processing circuit 60 of FIG. 1 is shown in greater detail in FIG. 2. The outputs of the pick-up toroids 54, 56 are applied to the preamplifiers 64, 66. The signals from the preamplifiers 64, 66 are then applied to the negative and positive inputs of the differential amplifier 68. The output of the differential amplifier 68 is a signal that represents the difference between the positive and negative inputs. The differential signal is then successively applied to an active filter 70 and an a.c. coupled amplifier 72 before being applied to the synchronous detector 74.

In dealing with analog signals it is conventional to amplify and filter the signals prior to taking their difference so as to render the difference more readily discernable from the noise. The present inventors experimented with that approach but found that, surprisingly, in the present invention it is much better to form the difference first and then to filter and amplify the signal.

This curious result does have a reasonable explanation, although at the time of the invention the explanation was not apparent. Essentially, the explanation is that the signals from the pick-up toroids 54, 56 are sine waves whose amplitude (maximum excursion) measures the conductivity. If these sine waves were first amplified, the information-bearing portions of the sine waves (their peaks) would fall into the nonlinear portion of the response curve of the amplifier and hence the most crucial portion of the wave would be distorted, yielding inaccurate results. Particularly when the water softener 12 is in need of recharging, the difference in the maximum amplitude of the signals from the pick-up toroids 54 and 56 will be quite small and therefore more susceptible to degradation by distortion. In contrast, in the present invention the signals entering the preamplifiers 64, 66 are relatively small in magnitude and hence do not extend into the nonlinear portion of the response curves of the preamplifiers and consequently are not distorted. Thus, in the system of the present invention the information-bearing portions of the signal are preserved with high fidelity.

Rather than detect the signals from the toroids first and then calculate the difference in the detected analog signals, in accordance with the present invention the amplitude modulated signals are applied to the differential amplifier 68 which is an operational amplifier connected as a difference amplifier. Because the signals coming out of the pick-up toroids 54, 56 are induced by the same oscillator 58 they remain closely in phase and consequently the common mode rejection capability of the differential amplifier 68 is exploited advantageously.

The output of the differential amplifier 68 includes a sine wave but also includes undesired quadrature components believed to be caused by capacitive coupling and stray inductive coupling between the exciting toroids and the pick-up toroids. The output of the differential amplifier 68 may also include undesirable noise, and the latter is attenuated out by the active filter 70 which, however, does not eliminate the quadrature components because the active filter is tuned to the same frequency as the oscillator 58. The output of the active filter 70 is applied to the amplifier 72 which has a gain of 32 db and which provides a stage of a.c. coupling prior to the synchronous detector 74.

The synchronous detector 74 is gated by the 20 kilohertz signal supplied by the oscillator to the exciting toroids 38, 40, by way of the conductor 76. The synchronous detector passes only the peaks of the sine waves and does not pass the quadrature signals which are out of phase with the peaks. The portions of the input wave that are passed by the synchronous detector are then smoothed to provide the detected signal. The detected signal is then applied to the d.c. amplifier 78 which conditions it to drive the meter 62. The output of the d.c. amplifier 78 is also applied, in a preferred embodiment, to the alarm relay 80 which includes a manually set trip point to enable the operation of an alarm device when the effectiveness of the water softener falls below a preset level.

In other embodiments the sensing and signal processing portions of the system operate on non-flowing samples, in which case the transport delay 26, the valves 28, 30 and the parallel-flow heat exchanger 32 are not used. In still other embodiments, the oscillator is replaced by a source of excitation signals, such as pulses, bursts of alternating current, intermittently repetitive signals, and periodic signals. The active filter 70 must be tuned to a frequency compatible with the excitation signal used, but the differential amplifier 68 and the synchronous detector 74 remain as hallmarks of the present invention.

Further, it is recognized that the use of the system of the present invention is not limited to monitoring water softeners, but can be used to monitor any type of liquid-treatment apparatus that alters the conductivity of the liquid treated.

The system just described and shown in FIG. 2 senses the conductivity of a treated sample of water and of an untreated sample of water. The difference in the conductivities is measured and is taken as an indication of how well the water softener or other treatment apparatus is functioning. The system shown in FIG. 3 is particularly useful where the conductivity of only a single fractional flow is to be measured.

Figure 3:
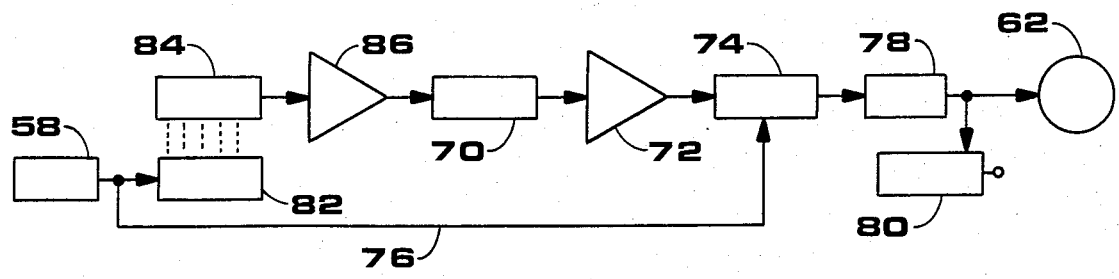

As shown in FIG. 3, when the conductivity of water from a single source is to be measured, only one exciting toroid 82 and one pick-up toroid 84 are used. The exciting toroid is driven by an oscillator 58, and an electrical signal is induced in the pick-up toroid 84. The strength of the signal indicates the conductivity of the liquid. The signal induced in the pick-up toroid 84 is applied to the preamplifier 86, the active filter 70 which is tuned to the frequency of the oscillator 58, and is then applied to the amplifier 72. The output of the amplifier 72 typically includes undesired quadrature components, and the present inventors have found that the synchronous detector 74 is particularly useful in eliminating the quadrature components. The synchronous detector 74 is gated by the output of the oscillator 58 so as to pass only the peaks of the applied signal. The detected signal output of the synchronous detector 74 is then applied to the d.c. amplifier 78 which produces an analog signal suitable for driving the meter 62 and operating the alarm relay 80. The system shown in FIG. 3 and just described is capable of measuring the conductivity of a liquid over a wide range of conductivity values with a high degree of accuracy.

Thus, there has been described in detail a preferred embodiment of the invention, and it is to be understood that additional embodiments thereof will be obvious to those skilled in the art. The embodiments described herein together with those additional embodiments are considered to be within the scope of the invention.

What is claimed is:

1. A system for assessing the effectiveness of a liquid-processing apparatus, such as a water softener, whose effectiveness is determinable from the difference between the conductivity of the liquid supplied to the liquid-processing apparatus and the conductivity of the liquid that has passed through the liquid-processing apparatus, said system comprising in combination:

source means for generating a common exciting signal $S_o$;

a first sensor connected to said source means for producing when energized by said common exciting signal $S_o$ a first conductivity signal $S_1$ related to the electrical conductivity of the liquid supplied to the liquid-processing apparatus;

a second sensor connected to said source means for producing when energized by said common exciting signal $S_o$ a second conductivity signal $S_2$ related to the electrical conductivity of the liquid that has passed through the liquid-processing apparatus;

circuit means connected to said first sensor and to said second sensor for producing a difference signal $S_3$ substantially equal to the difference between said first conductivity signal $S_1$ and said second conductivity signal $S_2$, but typically also including artifact components that are out of phase with the common exciting signal $S_o$; and, gated synchronous detector means connected to said circuit means and to said source means, enabled and synchronized by said common exciting signal $S_o$, and responsive to said difference signal $S_3$ for producing, when enabled by said common exciting signal $S_o$, a detected difference signal $S_4$ that is substantially unaffected by said artifact components, thereby making possible a more accurate determination of the difference between the conductivity of the liquid supplied to the liquid-processing apparatus and the conductivity of the liquid that has passed through the liquid-processing apparatus.

2. The system of claim 1 wherein said common means further comprise an oscillator.

3. The system of claim 2 wherein said common exciting signal $S_o$ is an alternating signal.

4. The system of claim 1 wherein said source means further comprise a pulse generator.

5. The system of claim 4 wherein said common exciting signal $S_o$ is a repetitive signal.

6. The system of claim 5 wherein said common exciting signal $S_o$ is a periodic signal.

7. A method for monitoring the effectiveness of a liquid-processing apparatus, such as a water softener, whose effectiveness is determinable from the difference between the conductivity of an incoming stream of liquid and the conductivity of an outgoing stream of liquid, said method comprising the steps of:

(a) generating a signal $S_o$;

(b) applying the signal $S_o$ to a first sensor which modifies the amplitude of the signal $S_o$ in relation to the conductivity of a sample of the incoming stream of liquid to obtain an amplitude modulated signal $S_1$;

(c) applying the signal $S_o$ to a second sensor which modifies the amplitude of the signal $S_o$ in relation to the conductivity of a sample of the outgoing stream of liquid to obtain an amplitude modulated signal $S_2$;

(d) producing a difference signal $S_3$ equal to the signal $S_1$ minus the signal $S_2$;

(e) applying the difference signal $S_3$ to a gated detector enabled by the signal $S_o$ to obtain an analog signal $S_4$ whose magnitude is related to the difference between the conductivity of the incoming stream of liquid and the conductivity of the outgoing stream of liquid.

8. The method of claim 7 wherein in step (a) the signal $S_o$ is repetitive.

9. The method of claim 7 wherein in step (a) the signal $S_o$ is periodic.

10. The method of claim 7 further comprising after step (d) and before step (e) the step of amplifying the difference signal $S_3$, and wherein in step (e) the amplified difference signal is applied to the gated detector.

11. A system for assessing the effectiveness of a liquid-processing apparatus, such as a water softener, whose effectiveness is determinable from the difference between the conductivity of the liquid supplied to the liquid-processing apparatus and the conductivity of the liquid that has passed through the liquid-processing apparatus, said system comprising in combination:

source means for generating a common exciting signal $S_o$;

a first sensor connected to said source means for producing when energized by said common exciting signal $S_o$ a first conductivity signal $S_1$ related to the electrical conductivity of the liquid supplied to the liquid-processing apparatus;

a second sensor connected to said source means for producing when energized by said common exciting signal $S_o$ second conductivity signal $S_2$ related to the electrical conductivity of the liquid that has passed through the liquid-processing apparatus;

circuit means connected to said first sensor and to said second sensor for producing a difference signal $S_3$ substantially equal to the difference between said first conductivity signal $S_1$ and said second conductivity signal $S_2$, but typically also including artifact components that are out of phase with the common exciting signal $S_o$; and, gated synchronous detector means connected to said circuit means and to said source means, enabled and synchronized by said common exciting signal $S_o$, and responsive to said difference signal $S_3$ for producing, when enabled by said common exciting signal $S_o$ a detected difference signal $S_4$ that is substantially unaffected by said artifact components, thereby making possible a more accurate determination of the difference between the conductivity of the liquid supplied to the liquid-processing apparatus and the conductivity of the liquid that has passed through the liquid-processing apparatus;

wherein at least one of said first sensor and said second sensor further include:

a first electrode and a second electrode, spaced apart and electrically in contact with the liquid so that a first conductive path through the liquid connects said first electrode and said second electrode;

a conductor connecting and providing a second conductive path between said first electrode and said second electrode;

whereby there is defined a closed conductive loop passing in sequence from said first electrode along said first conductive path to said second electrode and from said second electrode along said conductor to said first electrode; and, two toroids linked by said closed conductive loop.

12. A method for monitoring the effectiveness of a liquid-processing apparatus, such as a water softener, whose effectiveness is determinable from the difference between the conductivity of an incoming stream of liquid and the conductivity of an outgoing stream of liquid, said method comprising the steps of:
 (a) delaying a fraction of the incoming stream of liquid for use as the sample of the incoming stream of liquid;
 (b) generating a signal $S_o$;
 (c) applying the signal $S_o$ to a first sensor which modifies the amplitude of the signal $S_o$ in relation to the conductivity of a sample of the incoming stream of liquid to obtain an amplitude modulated signal $S_1$;
 (d) applying the signal $S_o$ to a second sensor which modifies the amplitude of the signal $S_o$ in relation to the conductivity of a sample of the outgoing stream of liquid to obtain an amplitude modulated signal $S_2$;
 (e) producing a difference signal $S_3$ equal to the signal $S_1$ minus the signal $S_2$;
 (f) applying the difference signal $S_3$ to a gated detector enabled by the signal $S_o$ to obtain an analog signal $S_4$ whose magnitude is related to the difference between the conductivity of the incoming stream of liquid and the conductivity of the outgoing stream of liquid.

13. The method of claim 12 wherein the delaying step further comprises routing said fraction through an extended path, whereby said delaying results from the time required for said fraction to travel the extended path.

14. A method for monitoring the effectiveness of a liquid-processing apparatus, such as a water softener, whose effectiveness is determinable from the difference between the conductivity of a sample of an incoming stream of liquid and the conductivity of a sample of an outgoing stream of liquid, said method comprising the steps of:
 (a) equalizing substantially the temperature of the sample of the incoming stream of liquid and the temperature of the sample of the outgoing stream of liquid;
 (b) generating a signal $S_o$;
 (c) applying the signal $S_o$ to a first sensor which modifies the amplitude of the signal $S_o$ in relation to the conductivity of the sample of the incoming stream of liquid to obtain an amplitude modulated signal $S_1$;
 (d) applying the signal $S_o$ to a second sensor which modifies the amplitude of the signal $S_o$ in relation to the conductivity of the sample of the outgoing stream of liquid to obtain an amplitude modulated signal $S_2$;
 (e) producing a difference signal $S_3$ equal to the signal $S_1$ minus the signal $S_2$;
 (f) applying the difference signal $S_3$ to a gated detector enabled by the signal $S_o$ to obtain an analog signal $S_4$ whose magnitude is related to the difference between the conductivity of the incoming stream of liquid and the conductivity of the outgoing stream of liquid.

15. The method of claim 14 wherein step (a) further comprises routing the sample of the incoming stream of liquid and the sample of the outgoing stream of liquid through a parallel flow heater exchanger.

* * * * *